(12) United States Patent
Shinzato

(10) Patent No.: US 8,127,779 B2
(45) Date of Patent: Mar. 6, 2012

(54) DENTAL FLOSS HOLDER

(76) Inventor: Nelson Shinzato, São Paulo (BR)

( * ) Notice: Subject to any disclaimer, the term of this patent is extended or adjusted under 35 U.S.C. 154(b) by 804 days.

(21) Appl. No.: 12/160,600

(22) PCT Filed: Jan. 4, 2007

(86) PCT No.: PCT/BR2007/000005
§ 371 (c)(1),
(2), (4) Date: Jul. 11, 2008

(87) PCT Pub. No.: WO2007/079559
PCT Pub. Date: Jul. 19, 2007

(65) Prior Publication Data
US 2010/0163072 A1 Jul. 1, 2010

(30) Foreign Application Priority Data

Jan. 12, 2006 (BR) .................................. 8600037 U
Jan. 4, 2007 (BR) ................. PCT/BR2007/000005

(51) Int. Cl.
*A61C 15/00* (2006.01)
(52) U.S. Cl. ....................................... 132/326; 132/325
(58) Field of Classification Search .................. 132/309,
132/310, 312, 322, 323, 324, 325, 326, 327,
132/328, 329
See application file for complete search history.

(56) References Cited

U.S. PATENT DOCUMENTS

| | | | | |
|---|---|---|---|---|
| 5,613,508 A | * | 3/1997 | Bushman | 132/325 |
| 5,979,468 A | * | 11/1999 | Blake, III | 132/318 |
| 6,109,808 A | * | 8/2000 | Susini et al. | 401/78 |
| 6,874,509 B2 | * | 4/2005 | Bergman | 132/325 |
| 7,270,129 B1 | * | 9/2007 | Rehkemper | 132/322 |
| 2005/0000539 A1 | * | 1/2005 | Bergman et al. | 132/325 |
| 2005/0111905 A1 | * | 5/2005 | Glover | 401/278 |
| 2005/0211262 A1 | * | 9/2005 | Raab | 132/309 |

* cited by examiner

*Primary Examiner* — Todd Manahan
*Assistant Examiner* — Niyati D Shah
(74) *Attorney, Agent, or Firm* — Furr Law Firm; Jeffrey Furr, Esq.

(57) ABSTRACT

The utility model of a dental floss holder concerns a device to handle dental floss to clean the spaces between the teeth consisting of two interconnected but easily separable holder portions: Portion 1—U shape supporter is provided with a U supporter (1) with two folding legs, connecting part (2) with longitudinal groove (6) and external thread (7), a hole (3) in the rear leg, a groove (4) that goes externally from the end of the front leg to the fixed end of U supporter (1) to hold the dental floss in position during cleaning operation. Portion 2—Hollow grip provided with a fixed side with a longitudinal inner blade (8) and the rotating side with a rotary end (9) and an internal thread (10). These two portions constitute a mechanism that limits the maximum floss tension adjusted by the rotary end (9). The device can operate with a piece of floss or from a floss supplier (12) connected to the rotary end (9).

13 Claims, 3 Drawing Sheets

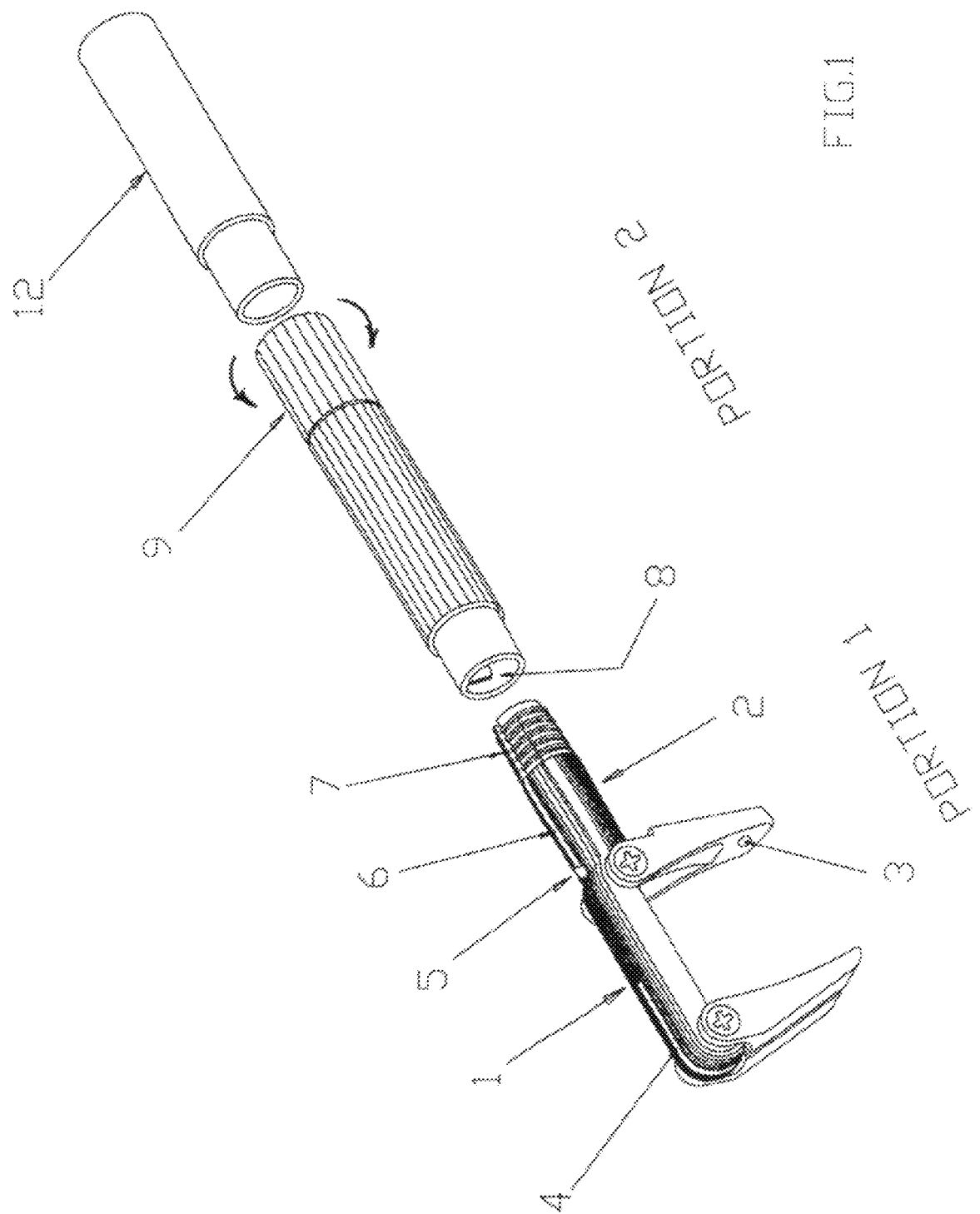

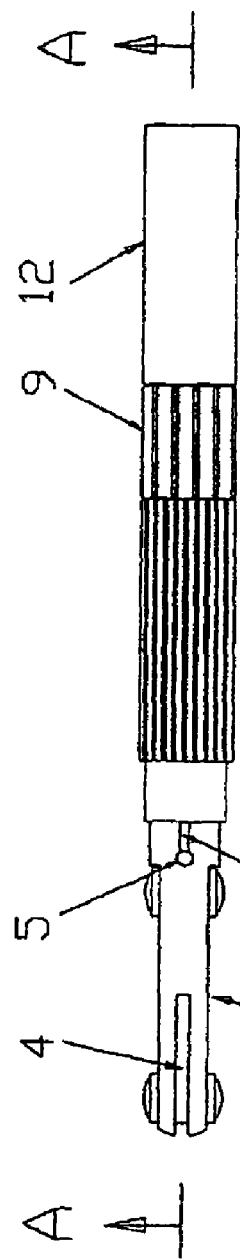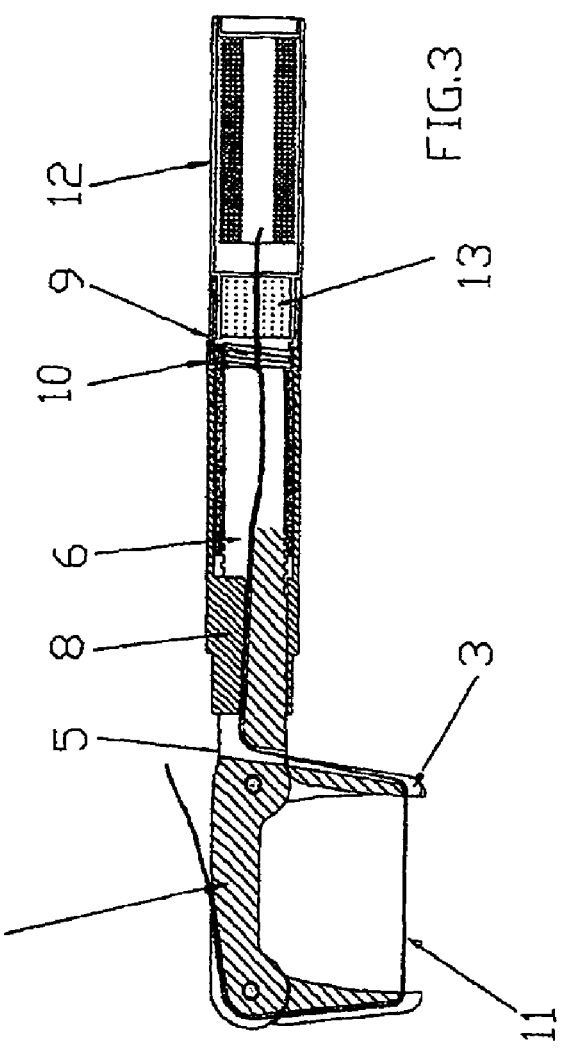

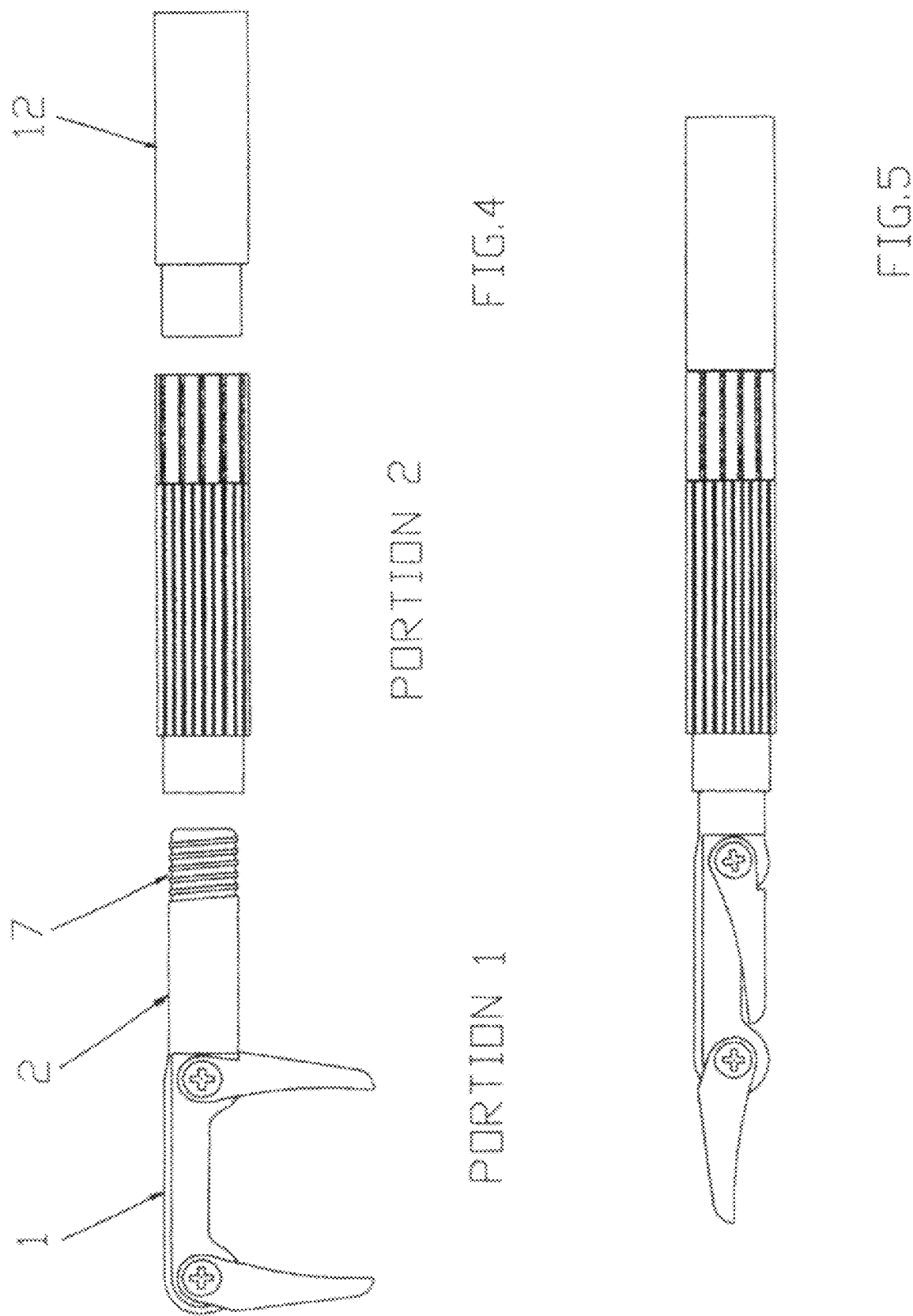

DENTAL FLOSS HOLDER

The dental floss holder, a utility model, concerns a device to handle dental floss to clean the spaces between the teeth effectively in a practical, simply and hygienic way.

To get an effective cleaning of the spaces between the teeth the floss have to wrap some portion of the tooth doing with an adequate controlled pressure on it during cleaning movement. In the traditional way, it is almost impossible to introduce the both fingers that control the floss tension inside the mouth. Other important condition to get a effective cleaning is to renew, as frequent as possible, the used portion of the floss. In the traditional way the renewal and getting new floss is done by winding the spent floss around the index finger of one hand and unwind the fresh portion of the floss pre-wound around the index finger of the other hand, or, if the fresh floss was only grasped with the fingers, doing it slide on the finger a required portion and start again the cleaning operation. The inconveniences of the traditional way of using dental floss are: Inadequate floss tension control specially when cleaning spaces between molar teeth; the introduction of the fingers into the mouth; the vulnerability of fresh floss portion contaminations from user's unclean fingers or surrounding environment; finger's pain during cleaning operation demotivating people to use this important way of teeth care.

It is therefore an objective of this utility model to provide a dental floss holder that may be manually operated, single-handedly, straightforward in its construction and operation, without having to put fingers into the mouth, and which may be effective in cleaning of the spaces between all the teeth.

The dental floss holder consisting of two interconnected but easily separable holder portions: U shape supporter and a hollow grip. The hollow grip rear part is composed of a rotary end used to adjust the maximum required floss tension.

These two portions constitute a mechanism which limits the maximum tension of the floss without its sliding, adjusted from the rotary end. The required length of the dental floss between the two U supporter legs, where the cleaning take place, is given by position and curvature of the index finger that keeps the spent floss wound around it, while the others fingers of the same hand grip firmly the device. The required dental floss pressure on the tooth is done by lateral force of the user's hand when doing cleaning movement.

The renewal of the spent floss portion from the U shape supporter is done by holding the grip with another hand, and that, pulling the end of the floss wound around the finger firmly and forth in a longitudinal direction of the device enough to wind more one turn. If the user wants to get more floss with a minimum force application, it may be done by "turning on" the rotary end to "loose" the floss, and after that, "turning off" the rotary end to clamp the floss again. During cleaning operation the floss tension transmitted to the finger is greatly reduced by the friction between the floss and groove's surfaces where it passes through.

The dental floss holder can operate with a piece of floss of required length, as in the traditional way, or operate with a floss supplier connected to the rotary end of the hollow grip.

The floss reel containers orifice from where the floss is drawn out has a restrictive passage of elastomeric material to keep the fresh floss protected from contamination.

As the dental floss passes through inside the grip there is no hand contact with the remainder portion during cleaning and renewal operations.

BRIEF DESCRIPTION OF THE DRAWINGS

The utility model, together with its objects and advantages, may be best understood by reference to the following description, taken in conjunction with the followings drawings, in which:

FIG. 1 shows a perspective view of a floss holder after separation of the two portions (Portion 1 and Portion 2) and the floss supplier.

FIG. 2 shows a top view of the floss holder with the two portions (Portion 1 and Portion 2) and with the floss supplier connected.

FIG. 3 shows a longitudinal-section view, taken along line A-A in FIG. 2 showing the floss in its operation position with the limiting tension control mechanism and a floss supplier.

FIG. 4 shows a side view of the floss holder after separation of the two portions (Portion 1 and Portion 2) and the floss supplier.

FIG. 5 shows a side view of the floss holder with the two portions (Portion 1 with retracted folding legs and Portion 2) and with the floss supplier connected.

DETAILED DESCRIPTION OF THE DRAWINGS

Relating to these figures they can be observed: Portion 1—U shape supporter is provided with a U supporter (1) with two folding legs, a connecting part (2), a hole (3) in the rear leg, a groove (4) that goes externally from the end of front leg until the fixed end of U supporter (1) to hold the dental floss in position during cleaning operation, a longitudinal groove (6) with its depth decreasing from the threaded end (7) to the hole (5) of the connecting part (2).

Portion 2—Hollow grip has a fixed side and a rotating side. The fixed side is provided with a longitudinal inner blade (8) with its height increasing from the fixed end to the other side.

The rotating side is provided with a rotary end (9) and an internal thread (10).

To connect Portion 1 to Portion 2 the blade (8) slides inside the groove (6) where the dental floss passes through. Depending on a greater or lesser pressure that the dental floss (11) is submitted it requires greater or lesser tension to slide. This pressure is given by how deep is the coupling between blade (8) and groove (6) controlled by the rotary end (9) that gives the penetration grade between the threads (7) (10).

The dental floss holder may be of a rigid material such as a hard plastic like ABS or polypropylene that can be easily molded and glued or melted to the illustrated shape. It is preferred that the surface of the gripping portion of the holder and the regulator be formed, for example, from thermoplastic elastomers included a gripping texture.

To prepare the dental floss holder to clean the spaces between the teeth the floss (11) is passed first through the Portion 2, then to the hole (5) of connecting part (2), then, keeping the dental floss tensioned to make sure that the floss lies the bottom of the groove (6) get coupling doing the blade (8) slides the groove (6). To fix the Portion 1 to Portion 2, the rotary end (9) is turned two or tree times to screw the threads (7) (10), then the floss (11) is passed through the hole (3) provided at the end of the rear leg of U supporter (1), and holding the grip with the hand that does not go work, the end of the floss is wound two or three turns around the proper finger of the another hand, and it is pulled straight doing the required tension adjustments with the rotary end (9), then the floss (11) is passed through the groove (4), provided from the end of the front leg until the fixed end of U supporter (1), and finally, the dental floss holder is griped with a proper hand to clean the spaces between the teeth.

The dental floss holder can operate with a piece of floss of required length, as in the traditional way, or operate with a floss supplier (12) connected to the rotary end (9) of the hollow grip.

This is a preferred alternative and differs substantially from the earlier application (MU-8600037-3) by its U supporter's folding legs. With this U shape design it may be contained in a tubular cap with the same diameter of the griping portion, then, like a pencil, easy to carry it.

The invention claimed is:

1. A dental floss holder is characterized by two interconnected but separable holder portions, U shape supporter (Portion 1) and a hollow grip (Portion 2), the U shape supporter is provided with a U supporter (1) with two folding legs, a connecting part (2), a hole (3) in a rear leg, a groove (4) that goes externally from an end of front leg until a fixed end of U supporter (1) to hold dental floss in position during cleaning operation, a longitudinal groove (6) with its depth decreasing from a threaded end (7) to a hole (5) of the connecting part (2), with the hollow grip (Portion 2) composed of a fixed side and a rotating side, and a maximum tension control mechanism is provided with a blade (8) on the fixed side of the hollow grip with its height increasing from the fixed side to the other side, a groove (6) with its depth decreasing from the threaded end (7) to the hole (5), external (7) and internal threads (10) and a rotary end (9) to adjust the maximum floss tension with the tension created by how deep is the coupling between blade (8) and groove (6) which is controlled by the rotary end (9) that gives a penetration grade between the threads.

2. Dental floss holder in accordance with claim 1, further characterized is that it can operate with a piece of floss from any required length as in the traditional way or from a continuous feeding from a floss supplier (12) connected to the rotary end (9).

3. Dental floss holder in accordance with claim 1, further characterized is that it connects a floss supplier (12), at the hollow grip's rotary end (9).

4. Dental floss holder in accordance with claim 1, further characterized is that it keeps dental floss passing through inside the grip.

5. Dental floss holder in accordance with claim 1, further characterized is that it allows renewal of the dental floss from the U supporter (1), without any hand contact with the remainder portion of the floss during cleaning operation.

6. A dental floss holder is characterized by two interconnected but separable holder portions, U shape supporter (Portion 1) and a hollow grip (Portion 2) with the U shape supporter provided with a U supporter (1) with two folding legs, a connecting part (2), a hole (3) in a rear leg, a groove (4) that goes externally from an end of front leg until a fixed end of U supporter (I) to hold dental floss in position during cleaning operation, a longitudinal groove (6) with its depth decreasing from a threaded end (7) to a hole (5) of the connecting part (2), with a hollow grip (Portion 2) composed of a fixed side and a rotating side further characterized is that it can operate with a piece of floss from any required length as in the traditional way or from a continuous feeding from a floss supplier (12) connected to a rotary end (9), with a maximum tension limit being adjusted from the rotary end (9) of the hollow grip with a maximum tension control mechanism provided with a blade (8) with its height increasing from the fixed side, a groove (6) with its depth decreasing from the threaded end (7) to the hole (5), external (7) and internal threads (10) and the rotary end (9) to adjust the maximum floss tension with the tension created by how deep is the coupling between blade (8) and groove (6) which is controlled by the rotary end (9) that gives a penetration grade between the threads.

7. Dental floss holder in accordance with claim 6, further characterized is that it connects a floss supplier (12), at the hollow grip's rotary end (9).

8. Dental floss holder in accordance with claim 6, further characterized is that it keeps dental floss passing through inside the grip.

9. Dental floss holder in accordance with claim 6, further characterized is that it allows renewal of the dental floss from the U supporter (1), without any hand contact with the remainder portion of the floss during cleaning operation.

10. A dental floss holder is characterized by two interconnected but separable holder portions. U shape supporter (Portion 1) and a hollow grip (Portion 2), with the U shape supporter provided with a U supporter (1) with two folding legs, a connecting part (2), a hole (3) in a rear leg, a groove (4) that goes externally from an end of front leg until a fixed end of U supporter (1) to hold dental floss in position during cleaning operation, a longitudinal groove (6) with its depth decreasing from a threaded end (7) to a hole (5) of the connecting part (2), with the hollow grip (Portion 2) composed of a fixed side and a rotating side, with a maximum tension limit adjusted from a rotary end (9) of the hollow grip and that a maximum tension control mechanism is provided with a blade (8) with its height increasing from the fixed side, a groove (6) with its depth decreasing from the threaded end (7) to the hole (5), external (7) and internal threads (10) and the rotary end (9) to adjust the maximum floss tension with the tension created by how deep is the coupling between blade (8) and groove (6) which is controlled by the rotary end (9) that gives a penetration grade between the threads.

11. Dental floss holder in accordance with claim 10, further characterized is that it connects a floss supplier (12), at the hollow grip's rotary end (9).

12. Dental floss holder in accordance with claim 10, further characterized is that it keeps dental floss passing through inside the grip.

13. Dental floss holder in accordance with claim 10, further characterized is that it allows renewal of the dental floss from the U supporter (1), without any hand contact with the remainder portion of the floss during cleaning operation.

* * * * *